(12) United States Patent
St. George et al.

(10) Patent No.: US 8,926,503 B2
(45) Date of Patent: *Jan. 6, 2015

(54) LIGHT SOURCE POWER BASED ON PREDETERMINED SENSED CONDITION

(71) Applicant: Gyrus ACMI, Inc., Southborough, MA (US)

(72) Inventors: Lawrence J. St. George, Sudbury, MA (US); Christopher A. Cook, New York, NY (US)

(73) Assignee: Gyrus ACMI, Inc., Southborough, MA (US)

( * ) Notice: Subject to any disclaimer, the term of this patent is extended or adjusted under 35 U.S.C. 154(b) by 27 days.

This patent is subject to a terminal disclaimer.

(21) Appl. No.: 14/070,865

(22) Filed: Nov. 4, 2013

(65) Prior Publication Data

US 2014/0058198 A1 Feb. 27, 2014

Related U.S. Application Data

(60) Continuation of application No. 13/755,458, filed on Jan. 13, 2013, now Pat. No. 8,591,408, which is a
(Continued)

(51) Int. Cl.
| | |
|---|---|
| *A61B 1/06* | (2006.01) |
| *A61B 1/00* | (2006.01) |
| *A61B 1/04* | (2006.01) |
| *A61B 1/12* | (2006.01) |
| *A61B 1/05* | (2006.01) |
| *H04N 7/18* | (2006.01) |

(52) U.S. Cl.
CPC ......... *A61B 1/00006* (2013.01); *A61B 1/00032* (2013.01); *A61B 1/0684* (2013.01); *A61B 1/00025* (2013.01); *A61B 1/00036* (2013.01); *A61B 1/00009* (2013.01); *A61B 2560/0209* (2013.01); *A61B 1/128* (2013.01); *A61B 1/05* (2013.01); *H04N 7/18* (2013.01); *A61B 1/0676* (2013.01)
USPC ............................ 600/178; 600/160; 600/118

(58) Field of Classification Search
CPC .............. A61B 1/00; A61B 1/04; A61B 1/06; A61B 1/00006; A61B 1/00009; A61B 1/00025; A61B 1/00036; A61B 1/00062; A61B 1/05; A61B 1/128
USPC .............. 600/178–180; 362/6, 574, 580, 276, 362/294, 372, 373
See application file for complete search history.

(56) References Cited

U.S. PATENT DOCUMENTS

| | | |
|---|---|---|
| 3,712,984 A | 1/1973 | Lienhard |
| 4,198,960 A | 4/1980 | Utsugi |

(Continued)

FOREIGN PATENT DOCUMENTS

| | | |
|---|---|---|
| EP | 0027361 | 4/1981 |
| EP | 0355996 | 2/1990 |

(Continued)

OTHER PUBLICATIONS

Japanese-language Office Action dated Feb. 28, 2012, issued by the Japanese Patent Office in Japanese Application No. 2008-1062393, 4 pages.

(Continued)

*Primary Examiner* — Anhtuan T Nguyen
*Assistant Examiner* — William Chou
(74) *Attorney, Agent, or Firm* — The Dobrusin Law Firm, P.C.

(57) ABSTRACT

A medical instrument having a lighting system for illuminating a target area, the system comprising a light source and associated power controller, the system being configured to move from a first illumination mode to a second illumination mode based on a sensed or determined changed condition, such as predetermined temperature and/or change in a scene or brightness signal, or lack of change, from an image sensor that may be associated with the instrument.

20 Claims, 8 Drawing Sheets

Related U.S. Application Data division of application No. 12/104,382, filed on Apr. 16, 2008, now Pat. No. 8,372,003.

(60) Provisional application No. 60/912,329, filed on Apr. 17, 2007.

(56) References Cited

U.S. PATENT DOCUMENTS

| | | | |
|---|---|---|---|
| 4,281,910 A * | 8/1981 | Takayama | 396/17 |
| 4,402,311 A | 9/1983 | Hattori | |
| 4,567,880 A | 2/1986 | Goodman | |
| 4,573,450 A | 3/1986 | Arakawa | |
| 4,602,281 A | 7/1986 | Nagasaki et al. | |
| 4,675,777 A | 6/1987 | Watrous | |
| 4,682,219 A | 7/1987 | Arakawa | |
| 4,685,449 A | 8/1987 | Bonnet | |
| 4,692,608 A | 9/1987 | Cooper et al. | |
| 4,809,680 A | 3/1989 | Yabe | |
| 4,832,003 A | 5/1989 | Yabe | |
| 4,873,572 A | 10/1989 | Miyazaki et al. | |
| 4,884,133 A | 11/1989 | Kanno et al. | |
| 4,884,279 A | 11/1989 | Odagiri | |
| 4,911,148 A | 3/1990 | Sosnowski et al. | |
| 4,925,445 A | 5/1990 | Sakamoto et al. | |
| 5,040,068 A | 8/1991 | Parulski et al. | |
| 5,178,130 A | 1/1993 | Kaiya | |
| 5,187,572 A | 2/1993 | Nakamura et al. | |
| 5,192,286 A | 3/1993 | Phan et al. | |
| 5,301,061 A | 4/1994 | Nakada et al. | |
| 5,307,803 A | 5/1994 | Matsuura et al. | |
| 5,325,847 A | 7/1994 | Matsuno | |
| 5,402,768 A | 4/1995 | Adair | |
| 5,402,769 A | 4/1995 | Tsuji | |
| 5,430,475 A | 7/1995 | Goto et al. | |
| 5,543,831 A * | 8/1996 | Tsuji et al. | 348/65 |
| 5,573,493 A | 11/1996 | Sauer et al. | |
| 5,598,205 A | 1/1997 | Nishioka | |
| 5,607,419 A | 3/1997 | Amplatz et al. | |
| 5,647,840 A * | 7/1997 | D'Amelio et al. | 600/169 |
| 5,704,892 A | 1/1998 | Adair | |
| 5,817,015 A | 10/1998 | Adair | |
| 5,846,183 A | 12/1998 | Chilcoat | |
| 5,850,496 A | 12/1998 | Bellahsene et al. | |
| 5,857,961 A | 1/1999 | Vanden Hoek et al. | |
| 5,940,126 A | 8/1999 | Kimura | |
| 5,941,818 A | 8/1999 | Hori et al. | |
| 5,957,834 A | 9/1999 | Mochida | |
| 6,124,883 A | 9/2000 | Suzuki et al. | |
| 6,142,930 A | 11/2000 | Ito et al. | |
| 6,184,923 B1 | 2/2001 | Miyazaki | |
| 6,206,825 B1 | 3/2001 | Tsuyuki | |
| 6,260,994 B1 | 7/2001 | Matsumoto et al. | |
| 6,331,156 B1 | 12/2001 | Haefele et al. | |
| 6,352,531 B1 | 3/2002 | O'Conner et al. | |
| 6,409,658 B1 | 6/2002 | Mitsumori | |
| 6,414,710 B1 | 7/2002 | Takahashi et al. | |
| 6,428,469 B1 | 8/2002 | Iddan et al. | |
| 6,449,006 B1 | 9/2002 | Shipp | |
| 6,459,919 B1 | 10/2002 | Lys et al. | |
| 6,468,204 B2 | 10/2002 | Sendai et al. | |
| 6,547,721 B1 | 4/2003 | Higuma et al. | |
| 6,659,940 B2 | 12/2003 | Adler | |
| 6,796,939 B1 * | 9/2004 | Konomura et al. | 600/179 |
| 6,831,679 B1 | 12/2004 | Olsson et al. | |
| 6,929,600 B2 * | 8/2005 | Hill | 600/120 |
| 6,976,956 B2 | 12/2005 | Takahashi et al. | |
| 6,994,667 B2 | 2/2006 | Singh | |
| 7,030,904 B2 | 4/2006 | Adair et al. | |
| 7,063,663 B2 | 6/2006 | Kazakevich et al. | |
| 7,101,379 B2 | 9/2006 | Gregory, Jr. et al. | |
| 7,214,183 B2 | 5/2007 | Miyake | |
| 7,241,262 B2 | 7/2007 | Adler et al. | |
| 7,413,543 B2 | 8/2008 | Banik et al. | |
| 7,479,106 B2 | 1/2009 | Banik et al. | |
| 7,559,892 B2 | 7/2009 | Adler et al. | |
| 7,591,783 B2 | 9/2009 | Boulais et al. | |
| 7,668,450 B2 | 2/2010 | Todd et al. | |
| 7,938,774 B2 | 5/2011 | Segawa | |
| 7,955,255 B2 | 6/2011 | Boulais et al. | |
| 2001/0031912 A1 | 10/2001 | Adler | |
| 2001/0040211 A1 | 11/2001 | Nagaoka | |
| 2001/0044571 A1 | 11/2001 | Mitsumori | |
| 2002/0013512 A1 | 1/2002 | Sendai et al. | |
| 2002/0154215 A1 | 10/2002 | Schechterman et al. | |
| 2002/0177750 A1 | 11/2002 | Pilvisto | |
| 2002/0188175 A1 | 12/2002 | Levine et al. | |
| 2003/0009086 A1 | 1/2003 | Black et al. | |
| 2003/0088254 A1 | 5/2003 | Gregory et al. | |
| 2003/0142753 A1 | 7/2003 | Gunday | |
| 2004/0034311 A1 | 2/2004 | Michalcik | |
| 2004/0039250 A1 | 2/2004 | Tholfsen et al. | |
| 2004/0090638 A1 * | 5/2004 | Babayoff et al. | 356/609 |
| 2004/0109488 A1 * | 6/2004 | Glukhovsky et al. | 374/120 |
| 2004/0111012 A1 | 6/2004 | Whitman | |
| 2004/0133075 A1 | 7/2004 | Motoki et al. | |
| 2004/0140425 A1 | 7/2004 | Lizuka et al. | |
| 2004/0230097 A1 | 11/2004 | Stefanchik et al. | |
| 2004/0242962 A1 | 12/2004 | Uchiyama | |
| 2004/0249246 A1 | 12/2004 | Campos | |
| 2005/0075538 A1 | 4/2005 | Banik et al. | |
| 2005/0080342 A1 | 4/2005 | Gilreath et al. | |
| 2005/0096502 A1 | 5/2005 | Khalili | |
| 2005/0119527 A1 | 6/2005 | Banik et al. | |
| 2005/0250983 A1 | 11/2005 | Tremaglio et al. | |
| 2005/0267328 A1 | 12/2005 | Blumzvig et al. | |
| 2005/0277810 A1 | 12/2005 | Irion | |
| 2006/0055793 A1 | 3/2006 | Adler et al. | |
| 2006/0173242 A1 | 8/2006 | Navok et al. | |
| 2006/0183976 A1 | 8/2006 | Adler et al. | |
| 2007/0177009 A1 | 8/2007 | Bayer et al. | |
| 2007/0185386 A1 | 8/2007 | Cheng | |
| 2008/0108869 A1 * | 5/2008 | Sanders et al. | 600/109 |
| 2008/0183043 A1 | 7/2008 | Spinnler et al. | |
| 2009/0036744 A1 | 2/2009 | Vayser | |

FOREIGN PATENT DOCUMENTS

| | | |
|---|---|---|
| EP | 0573746 | 12/1993 |
| EP | 0647425 A1 | 4/1995 |
| EP | 1202767 | 7/2000 |
| JP | 60104915 | 6/1985 |
| JP | 61281680 | 12/1986 |
| JP | 62-35314 | 3/1987 |
| JP | 63136781 | 6/1988 |
| JP | 63210813 | 9/1988 |
| JP | 63-052728 A | 10/1988 |
| JP | 4-36716 | 2/1992 |
| JP | 04236934 | 8/1992 |
| JP | 05142484 | 6/1993 |
| JP | 06335450 | 12/1994 |
| JP | 7209590 | 8/1995 |
| JP | 07275200 | 10/1995 |
| JP | 08024219 | 1/1996 |
| JP | 08050251 | 2/1996 |
| JP | 08114755 | 5/1996 |
| JP | 6366525 | 3/1998 |
| JP | 10151105 | 6/1998 |
| JP | 2000139821 | 5/2000 |
| JP | 2000147389 | 5/2000 |
| JP | 2000171727 | 6/2000 |
| JP | 2000206422 | 7/2000 |
| JP | 200234910 | 2/2002 |
| JP | 200258633 | 2/2002 |
| JP | 200285345 | 3/2002 |
| JP | 2002508201 | 3/2002 |
| JP | 2005525896 | 9/2005 |
| JP | 2006000282 | 1/2006 |
| JP | 2006334076 | 12/2006 |
| JP | 2007044350 | 2/2007 |
| WO | WO9930610 | 6/1999 |
| WO | 0049448 | 8/2000 |
| WO | 0176452 | 10/2001 |
| WO | WO02078632 | 10/2002 |
| WO | 03013624 | 2/2003 |

(56) References Cited

FOREIGN PATENT DOCUMENTS

| WO | WO03028547 | 4/2003 |
|----|------------|--------|
| WO | WO03098913 | 11/2003 |
| WO | WO2006032013 | 3/2006 |
| WO | 2006/066022 | 6/2006 |

OTHER PUBLICATIONS

Office Action dated Dec. 12, 2011 from the Patent Office in Germany Patent Application No. 10392670.4, 9 pages.
Office Action dated Jun. 17, 2011 from the Patent Office of Japan in Japanese Patent Application No. 2004-506277; 5 pages. English translation included.
Japanese Office Action dated May 19, 2011, for Japanese Patent Application No. 2010-278712 (Japanese language); 6 pages total. (English translation included).
Japanese Office Action dated Apr. 26, 2011, for Japanese Patent Application No. 2008-106293 (Japanese language); 4 pages total. (Abridged English translation included).
Japanese Office Action dated Mar. 18, 2009, for corresponding Japanese patent application No. 2004-506277; English translation; 4 pages.
Japanese Office Action dated Dec. 22, 2009, for a related Japanese Patent Application No. 2004-506277; 11 pages. English translation included.
Final Office Action dated May 28, 2010 from related U.S. Appl. No. 10/514,607; 12 pages.
Non-Final Office Action dated Jul. 22, 2009 from related U.S. Appl. No. 10/514,607; 11 pages.
Non-Final Office Action dated Nov. 24, 2009 from related U.S. Appl. No. 10/514,607; 10 pages.
Japanese Office Action dated Jan. 25, 2011, for a related Japanese Patent Application No. 2004-506277; 9 pages. English translation included.
Japanese Office Action dated Aug. 17, 2010, for a related Japanese Patent Application No. 2004-506277; 6 pages. English translation included.
Kodak, "Shutter Operations for CCD and CMOS Image Sensors Revision 2.0" Dec. 17, 2003 http://www.kodak.com/global/plugins/acrobat/en/business/ISS/supportdocsShutterOperation.pdf—4 pages.
PCT International Search Report and Written Opinion dated Sep. 27, 2010 for related patent application No. PCT/US2010/040100, filed Jun. 25, 2010; 13 pages.
United States Patent and Trademark Office Final Office Action dated Nov. 9, 2010 for related U.S. Appl. No. 11/109,041, filed Apr. 18, 2005; 13 pages.
Examination Report from the German Patent and Trademark Office dated Jul. 12, 2010 for related German patent application No. 102008018931.6; informal English translation provided by German agent is included; 10 pages total.
U.S. Patent and Trademark Office Action dated May 22, 2009 for related U.S. Appl. No. 11/109,041, filed Apr. 18, 2005; 21 pages.
Applicant's response to U.S. Patent and Trademark Office Action dated May 22, 2009 for related U.S. Appl. No. 11/109,041. Response filed Aug. 19, 2009; 18 pages.
Kodak, Shutter Operations for CCD and CMOS Image Sensors Revision 2.0* Dec. 17, 2003 http://www.kodak.com/global/plugins/acrobat/en/business/ISS/supportdocsShutterOperation.pdf—4 pages.
PCT International Search Report and Written Opinion dated Sep. 27, 2010 for related U.S. Appl. No. PCT/US2010/040100, filed Jun. 25, 2010; 13 pages.

* cited by examiner

LIGHT SOURCE POWER BASED ON PREDETERMINED SENSED CONDITION

RELATED APPLICATIONS

This application claims the benefit of and priority to U.S. Provisional Application Ser. No. 60/912,329, filed Apr. 17, 2007, the contents of which are hereby incorporated by reference as if recited in full herein for all purposes.

BACKGROUND

The inventive subject matter generally relates to power control for a light source for a handheld medical instrument for intracorporeal use. The inventive subject matter particularly relates to solid state lighting sources, such as LEDs, used in an endoscope.

Although not limited to the use in an endoscope, the inventive subject matter will be illustrated by reference to endoscopic light systems, particularly those using electronic image sensors and LED light sources disposed on or in an endoscope.

In order to eliminate the heavy, bulky and awkward fiberoptic "light pipe" from a conventional light source (i.e., 300W Xenon), high-power, white LEDs are currently used as an endoscope light source. The LEDs are contained in the body of an digital endoscope. Such LEDs, while more efficient than a conventional light source, produce some significant heat when operating at a high light output. Accordingly, there is a need to control the temperature of the body of the endoscope to a maximum of about 40° C. to meet with operator comfort or safety requirements, and preferably to keep the instrument temperature even lower than that for operator comfort and confidence.

Current designs vary the output of the LEDs as part of the electronic exposure system and strive to keep the temperature below the prescribed limit by simply setting a maximum current limit. If the imaging system senses a situation with insufficient light, it increases LED output up to the maximum, if needed, and keeps it there if the scene still seems to be insufficiently lit. A drawback to the approach of a set maximum power to the LEDs to control the temperature is that the potential of using a higher LED output capability for short periods of time is compromised.

Another problem with current LED systems is their failure to intelligently adapt to state of activity. For example, it is not uncommon for an electronic endoscope to be placed on a table or cart and left for some period of time, with the end pointing toward objects much farther away than the designed operating distance of the endoscope, with lighting conditions which the endoscope will determine as insufficient. These conditions can set the LED drive to its maximum output, and the handle will heat up to the set maximum temperature. A user coming back to pick up the endoscope will sense a rather hot object.

Accordingly, there is a need for improved illumination systems with automated temperature control and intelligent adaptation to their state of activity.

SUMMARY

The inventive subject matter provides an improved system for managing power to an illumination source on board an instrument. In doing so, it addresses, among other things, the need for temperature management in an electronic endoscope, for example.

In certain embodiments, the inventive subject matter is directed to a medical instrument having a lighting system for illuminating a target area, the system comprising a light source for illuminating an intracorporeal target area and associated power controlled, the system being configured to move from a first illumination mode to a second illumination mode based on an input into the system of a predetermined changed condition such as whether or not the instrument is in active use. The medical instrument may be a handheld instrument and the light source is disposed within a housing that comprises the handle of the instrument. The medical instrument may be an endoscope having a solid-state light source on or in the instrument for illuminating a target area. The medical instrument may have a light source disposed in a handle portion of the instrument. The medical instrument may have a light source disposed in a distal insertion end of the instrument. The medical instrument may have an image sensor disposed within a distal insertion portion of the instrument. The medical instrument may be configured to adapt to a state of activity by sensing a predetermined change of scene or brightness or lack of change, and make a predetermined change in power to the light source based on the change or lack thereof in scene or brightness. The medical instrument may have a set of predetermined pixels in one or more image sensors that are designated for providing signals which are processed to determine whether there is a predetermined change in scene or brightness. The medical instrument may be configured to sense a predetermined change of temperature and make a predetermined change in power to the light source based on the change in temperature. The medical instrument may be battery powered. The medical instrument may be adapted to maintain the temperature of a surface of the instrument held or otherwise contacted by a user at a temperature of below about 40 degrees C. or some other predetermined safety or comfort temperature.

In other possible embodiments, the inventive subject matter is directed to a medical instrument, comprising an imaging system and an illumination system, the imaging system comprising a pixellated image sensor; and the illumination system comprising one or more solid-state lighting devices, the instrument being configured so that a state of activity of the instrument is determined by processing signals from one or more pixels in the image sensor, and a power mode for the instrument is determined according to an output of the processing. In the embodiments disclosed herein, the power mode may be a power setting for the illumination system. In the embodiments disclosed herein, the system may determine a state of inactivity of us based on processing of the signals and provides reduced power to the illumination system based on a predetermined period of inactivity. In the embodiments disclosed herein, the medical instrument may use any the input for determining a condition or state of use that comprises a signal from a piezoelectric sensor or an accelerometer associated with the instrument.

In yet another possible embodiment, the inventive subject matter is directed to a method of making a medical instrument, comprising disposing in a housing for a medical instrument an illumination system comprising one or more light sources; configuring the illumination system with a power controller that determines power to the light source according to a state of activity for the instrument; and configuring the instrument to determine state of activity according to processing of signals from an image sensor. In the method, the instrument may comprise an endoscope having the image sensor at a distal insertion end of a housing for the endoscope and solid state light source in the housing, the instrument being configured to reduce power to the light source after processing the signals to an output indicative of inactivity.

In addition to the medical instrument, the inventive subject matter extends to methods of using the instrument, systems thereof, and machine executable instructions in a storage media for implementing novel steps of power control, according to the inventive subject matter.

These and other embodiments are described in more detail in the following detailed descriptions and the figures.

The foregoing is not intended to be exhaustive list of embodiments and features of the present inventive concept. Persons skilled in the art are capable of appreciating other embodiments and features from the following detailed description in conjunction with the drawings.

BRIEF DESCRIPTION OF THE DRAWINGS

The following figures show embodiments according to the inventive subject matter, unless noted as showing prior art.

DETAILED DESCRIPTION

Representative embodiments according to the inventive subject matter are shown in FIGS. 1-7, wherein similar features share common reference numerals.

In one example embodiment of the inventive subject matter, a medical instrument such as an endoscope includes a temperature-sensing LED drive control to the system which will limit the power input to the LED based on keeping the handle temperature below the about 40° C. limit. This would allow higher output power from the LEDs for short periods of time if the handle temperature were below the maximum.

In another example embodiment of a medical instrument such as an endoscope includes an automatic power reduction mode based on (1) a self-timer; (2) detected scene changes; and/or (3) overall power output in order to address the situation where the endoscope is left alone for some period of time. This is a situation where the LED light source could run at a maximum due to insufficient scene light under the current design, but using the inventive subject matter reduces the LED output after a period of inactivity and thus the handle surface would be cooler at these times.

In other embodiments, a medical instrument may be configured with both a temperature sensing system and a scene change system. For example, one system could be a back-up or supplementation of the other.

In other embodiments a condition change other than a temperature or scene changed could be correlated with a power setting for the light source. For example, the handle of the instrument could include a piezoelectric sensor that could sense whether or not the instrument is being held, and power down the light source a predetermined degree if it is not. As another example, a solid-state accelerometer could be deployed to determine whether or not there has been a predetermined change in position of the instrument and determine power to the light source accordingly.

In the foregoing embodiment, a typical user configuration provides for reduction in power to the light source if there is an indication of inactivity, such as no change in scene, over a period of one to three minutes. A two minute period of inactivity leading to power reduction is a most typical configuration.

The following discussion introduces a basic, example hardware platform over which the inventive subject may be used. From this discussion, persons skilled in the art will appreciate how to adapt the platform for use in monitoring for changes in image data that correlate with a predetermined condition for adjusting the power level of an illumination source. The platform is illustrative and not intended to limit the scope of the inventive subject matter.

Figure 1A:
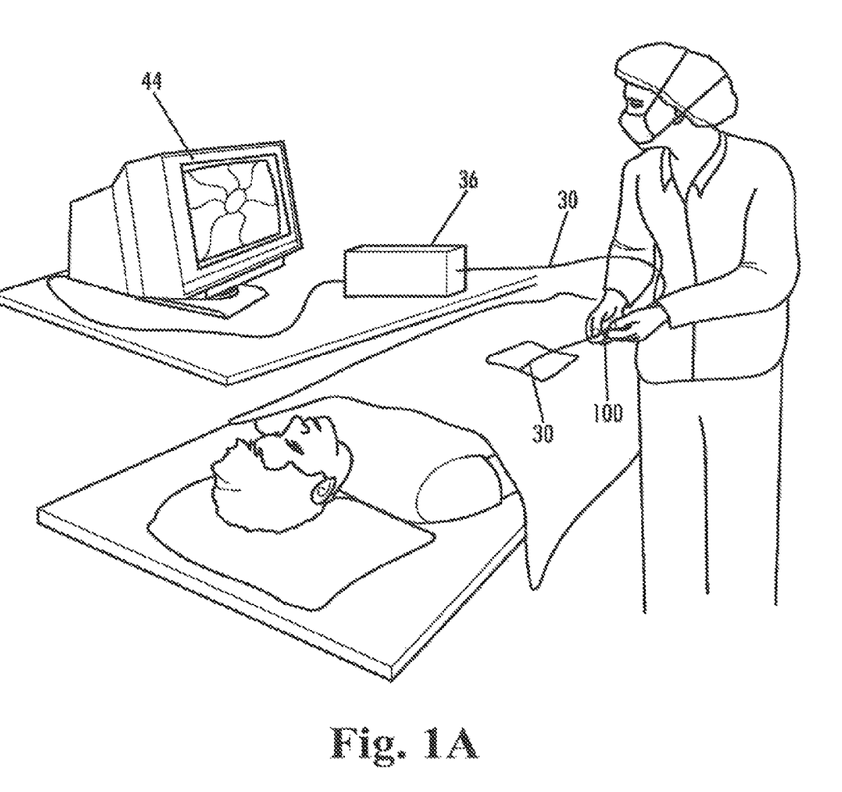
FIG. 1A is a schematic, pictorial illustration of a system for endoscopy, in accordance with a embodiment of the present invention.
Figure 1B:
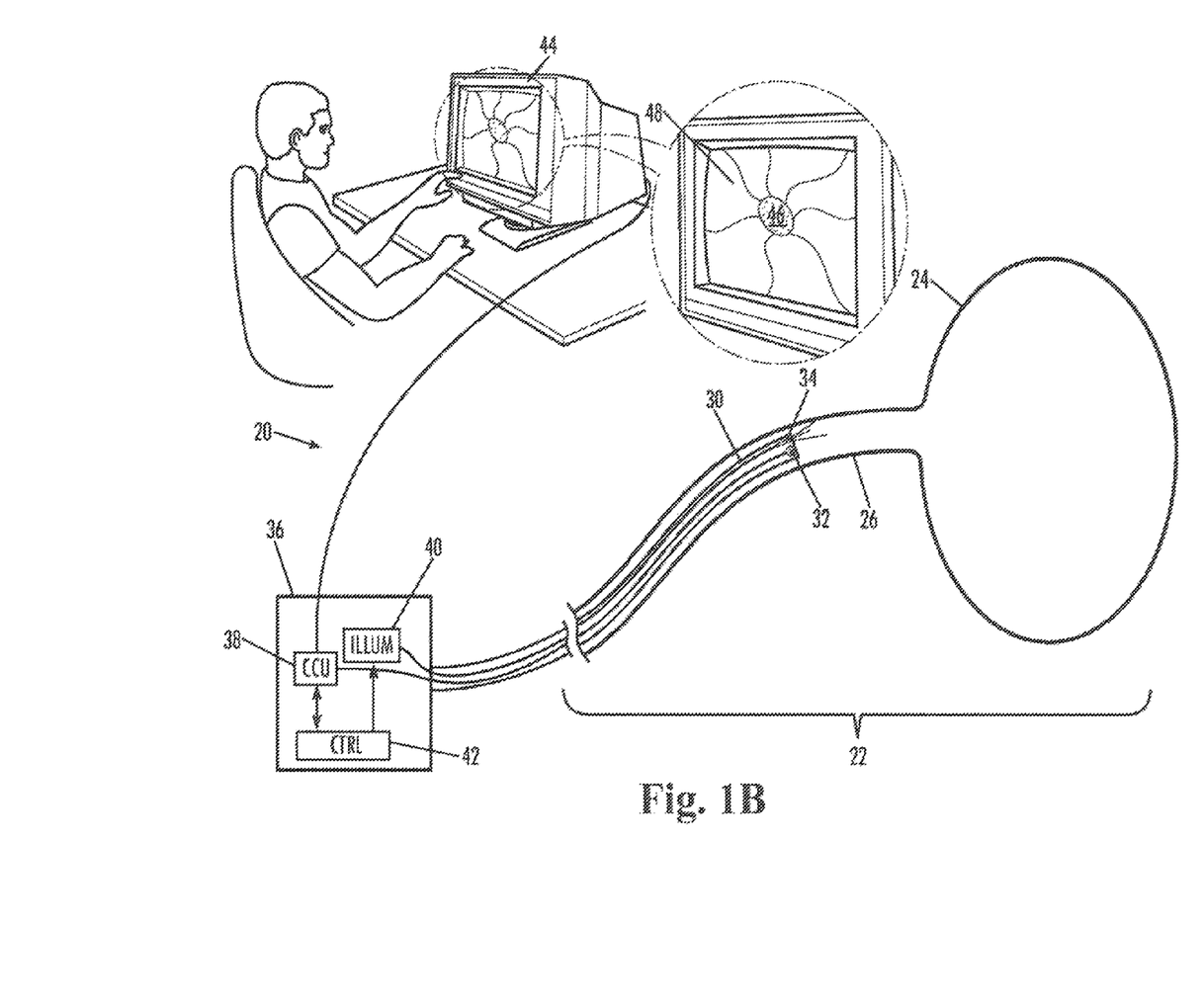
FIG. 1B is a schematic, pictorial illustration showing details of the system of FIG. 1A, in accordance with an embodiment of the present invention.

FIGS. 1A and 1B schematically illustrate a system 20 for endoscopic imaging of a body cavity 22, in accordance with an embodiment of the inventive subject matter. Cavity 22 represents a chamber 24, which is accessed through a lumen 26. Chamber 24, for example, may be the urinary bladder of a patient, in which case lumen 26 is the urethra. As another example, chamber 24 may be the stomach, in which case lumen 26 is the esophagus. The principles of the present invention are similarly applicable to other body cavities or passages, as will be apparent to those skilled in the art.

Furthermore, although the example embodiments described herein below relate specifically to endoscopic imaging, the principles of the present invention may also be applied to electronic imaging systems of other types.

System 20 comprises an endoscope insertion shaft or tube 30, having an image sensing assembly 32 and an illumination source 34 at its distal end. The endoscope includes a handle portion 100. As used herein, "handle" means any portion of the endoscope or other instrument grasped or in contact with a user. The detailed structure of the endoscope, and particularly of the assemblies at the distal end, may be as described in PCT patent publication WO 03/098913, for example, whose disclosure is in its entirety incorporated herein by reference. Image sensing assembly 32 typically comprises an image sensor, such as a CMOS or CCD image sensor, with suitable objective optics. In an alternative embodiment (not shown in the figures), the image sensing assembly is located at the proximal end of the insertion tube and is coupled to receive images from the distal end via a fiberoptic image guide or relay optics.

Illumination source 34 may be light source, such as an LED, located at the distal end of the endoscope insertion tube. Alternatively, the illumination source may be a fiberoptic light guide, with a connection to a suitable light source at the proximal end of the endoscope.

Insertion tube 30 may be coupled to a camera control unit (CCU) 36, which controls the functions of the endoscope and processes image signals generated by image sensing assembly 32. Typically, the CCU is remote from the endoscopic instrument. The coupling may be by physical conduits or wireless transmitters and receivers. The CCU typically is disposed in a console 36. The CCU 38 receives and processes the signals to produce a standard video output. CCU 38 may also output control signals to assembly 32 for controlling functions such as the shutter speed and gain of the image sensor. An optional illumination controller 40 in console 36 regulates the level of light that is output by distal illumination source 34. The functions of the CCU and illuminations controller are regulated by a control processor 42, using methods described herein below. Although the CCU, illumination controller and control processor are shown and described herein as separate functional units, for the sake of conceptual clarity, some or all of the functions of these elements may be integrated in a single processing circuit, comprising one or more integrated circuit chips.

Video images generated by CCU 38 are displayed on a video display device, such as a video monitor 44. In the situation illustrated in FIG. 1B, in which the distal end of insertion tube 30 is located with lumen 26, the displayed image typically is a dark central region 46, corresponding to the bore of the lumen, and a brighter peripheral region 48 showing the walls of the lumen. As the endoscope is advanced or withdrawn through the lumen, the overall brightness of these regions of the image changes slowly, if at all, since the topology and nature of the tissue viewed by image sensing assembly 32 do not change.

On the other hand, when the insertion tube enters chamber 24, the wall of the chamber will come into view. As the distal end of the insertion tube approaches the wall, the intensity of the light (flux per unit area) incident on the wall from illumination source 34 will increase approximately as the inverse square of the distance between the distal end and the wall. At the same time, the relative intensity of light reflected back from the wall and captured by sensor assembly 32 will also increase approximately as the inverse square of the distance. As a result, the brightness of the image captured by the image sensor will increase or decrease very abruptly as the distal end of the insertion tube moves toward or away from the chamber wall; roughly as the inverse fourth power of the distance. Methods of automated brightness control that are known in the art are generally incapable of keeping pace with such rapid brightness changes, leading to temporary loss of image visibility due to saturation or cutoff of all or part of the image. Control processor 42 may use a novel control method, based on the topology of cavity 22, in order to avoid this loss of image visibility. Details of this method are presented below with reference to FIG. 4.

Figure 2:
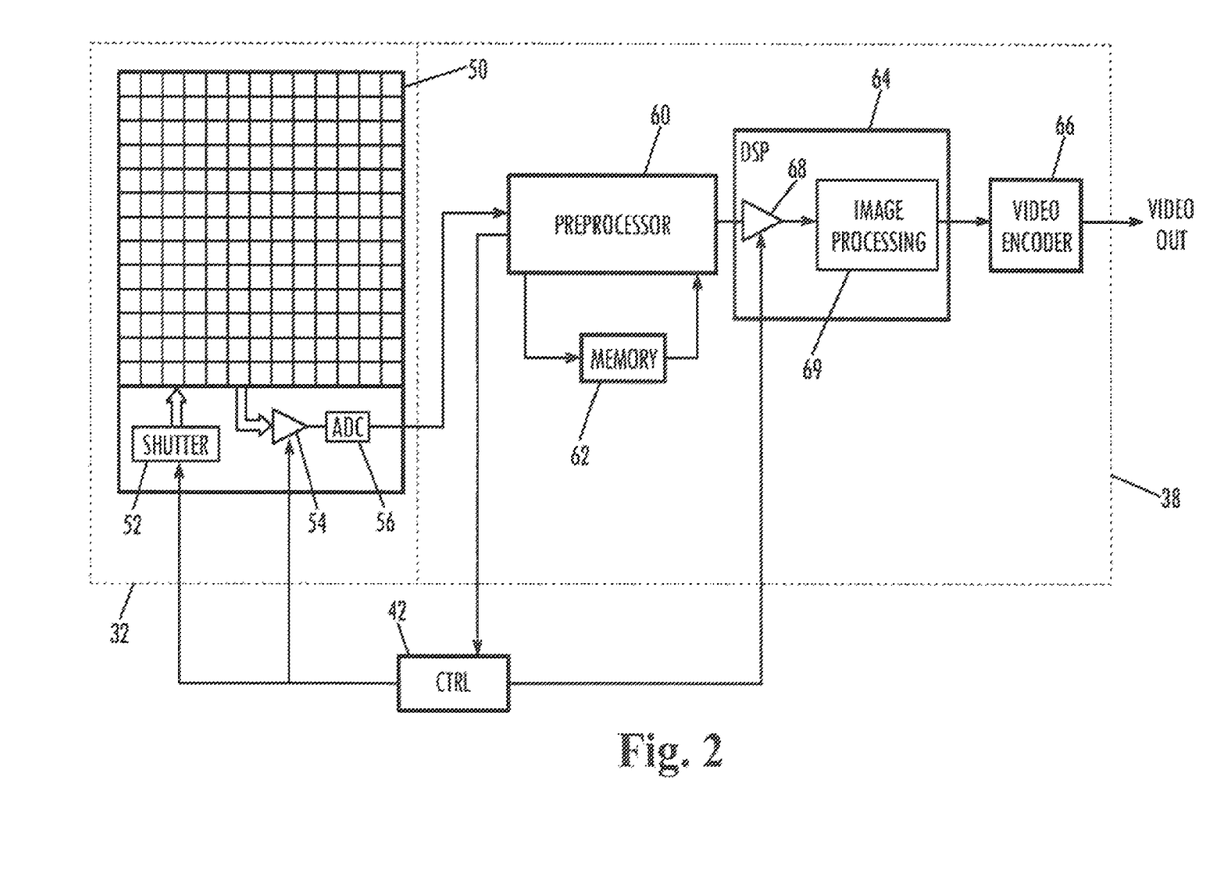
FIG. 2 is a block diagram that schematically shows circuitry for controlling image brightness, in accordance with an embodiment of the present invention.

FIG. 2 is a block diagram that schematically shows details of image sensing assembly 32 and console 36, including CCU 38, in accordance with an embodiment of the present invention. As noted above, the image sensing assembly comprises an image sensor 50, such as a CMOS image sensor. The image sensor chip in this case may include ancillary circuitry. For example, the ancillary circuitry may be any one or more of the following: an onboard electronic shutter control 52; output amplifier 54; and analog/digital converter (ADC) 56. Alternatively, some or all of these ancillary circuit elements may be located on a separate chip. Further alternatively, some of the ancillary circuitry, such as ADC 56, may be contained in CCU 38.

In this embodiment, a preprocessor 60 in CCU 38 receives the digitized sample stream that is output by image sensor 50. Typically, preprocessor 60 comprises an integrated logic array, such as a field programmable gate array (FPGA), which operates on the digitized samples to compute actual digital pixel values. A digital signal processor (DSP) 64 comprises a level adjuster 68, which scales the pixel values, and an image processing block 69. A video encoder 66 converts the stream of pixel values into a standard video output signal. Preprocessor 60 is coupled to a buffer memory 62, typically a dualport RAM buffer, in order to match input and output pixel rates and compensate for processing latency if necessary.

Control processor 42 also receives information regarding the output sample stream (or the actual sample stream itself) from preprocessor 60, and processes this information in order to determine appropriate settings of the sensor shutter speed and gain. Processor 42 then generates appropriate control inputs to sensor 50, either directly (as shown in this figure) or via CCU 38 (as shown in FIG. 1E). Additionally or alternatively, processor 42 generates a gain control output to DSP 64, for controlling the level of the output video signals. Typically, processor 42 comprises a general-purpose or embedded microprocessor, which is programmed in software to carry out the functions described herein.

Figure 3:
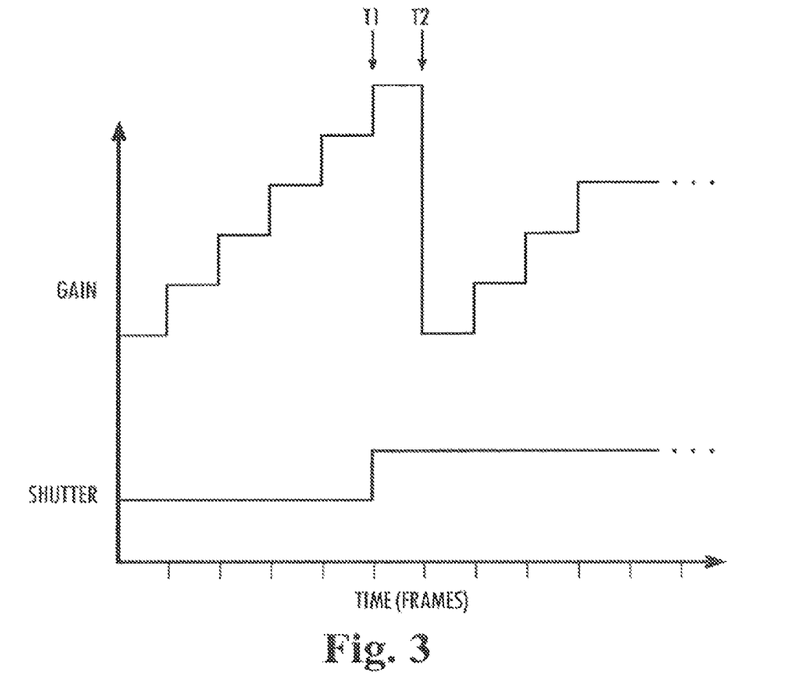
FIG. 3 is a timing diagram that schematically illustrates adjustments of gain and shutter speed in an electronic imaging system, in accordance with an embodiment of the present invention.

FIG. 3 is a timing diagram that schematically shows gain and shutter speed settings that are determined and applied by control processor 42, in accordance with an embodiment of the inventive subject matter. In this embodiment, it is assumed that the level of light that is incident on sensor 50 is gradually decreasing over time, requiring a concomitant increase in the exposure time provided by shutter control 52. In this simplified example, it is also assumed that illumination source 34 is already operating at full intensity, or that the intensity of the illumination source is fixed, so that illumination controller 40 cannot be used to adapt to the decreasing level of incident light. Alternatively, the control method exemplified by FIG. 3 may be modified to include control of illumination level, as will be apparent to those skilled in the art. Although this embodiment shows how processor 42 adapts to decreasing light level, the method used in this embodiment is similarly applicable in adaptation to increasing light level.

As noted above, image sensor 50 may be a CMOS sensor, which has a conventional rolling shutter. Rolling shutter operation is described, for example, in a Kodak application note entitled "Shutter Operations for CCD and CMOS Image Sensors" (Revision 2.0, Dec. 17, 2003), which is available at www.kodak.com/go/imagers and is incorporated herein by reference. This mode of operation introduces an inherent delay of at least one video frame between the time at which an image is captured and control processor 42 determines, based on the image, that a change in shutter speed is needed and the time at which the change is actually carried out by shutter control 52. In other words, if a frame n is captured, and after analyzing this frame, processor 42 signals shutter control 52 at the beginning of frame n+1 to increment the shutter period, the change in shutter speed will actually occur only in frame n+2.

In order to compensate for this delay, processor 42 applies a gain increase to the output of sensor 50 during frame n, roughly concurrent with instructing shutter control 52 to increase the shutter duration. In other words, as shown in FIG. 3, at time T1 processor 42 simultaneously signals shutter control 52 to increase the shutter duration (i.e., to increase the charge integration time of the elements of sensor 50) and increases the gain applied to the sensor output. One frame later, at time T2, processor 42 reduces the gain to compensate for the increased sensor signal level due to the increased shutter duration. In systems known in the art, the gain may be decreased simultaneously with the command to increase the shutter duration. In system 20, however, processor 42 first increases the gain, and then decreases the gain one frame later in order to account for the inherent delay of the rolling shutter in sensor 50.

The gain increase shown in FIG. 3 may be applied to output amplifier 54. Alternatively or additionally, control processor 42 may instruct DSP 64 to adjust the gain applied to the current frame in the output video signal. Processor 42 may compute the appropriate gain to apply to the current frame while the frame is held in memory 62, and may then instruct DSP 64 to apply this gain to the same, current frame using level adjuster 68, while instructing sensor 32 to apply the same gain change in amplifier 54, which will affect the next frame. This arrangement permits rapid gain adaptation in response to changes in the brightness of the image generated by sensor 50. Processor 42 then instructs shutter control 52 to increase the shutter duration and accordingly decreases the gain applied by the DSP in the next frame.

Figure 4:
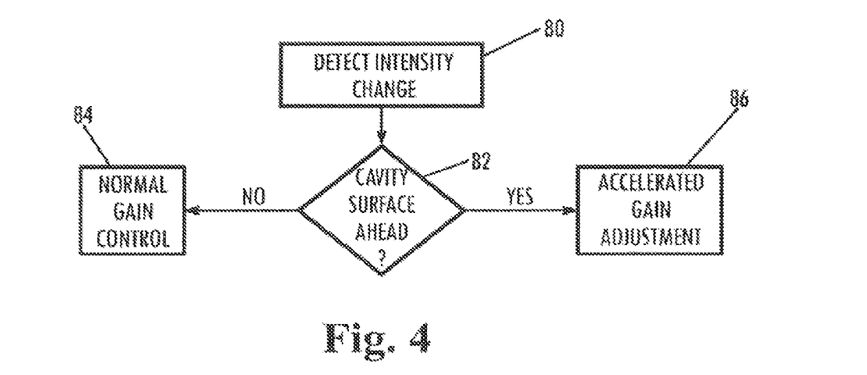
FIG. 4 is a flow chart that schematically illustrates a method for predictive control of image brightness, in accordance with an embodiment of the present invention.

FIG. 4 is a flow chart that schematically illustrates a method applied by processor 42 in controlling image brightness in system 20, in accordance with an embodiment of the present invention. The method is described, for the sake of simplicity, with reference to gain control, but the method may also be applied, alternatively or additionally, in controlling shutter speed and/or illumination intensity. The method is keyed to the topological characteristics of body cavity 22 (FIG. 1B), but the principles embodied in the method may alternatively be adapted for use in topologies of other types.

The method is initiated when control processor 42 detects a change in the image brightness level, at an intensity detection step 80. The change is typically due to an increase or decrease in the intensity of the light that is incident on image sensor 50. The change may be detected, for example, in terms of a change in the average the pixel values output by the image sensor or a change in certain histogram characteristics. The change may be global change, with respect to all the pixels in the image, or may be in one particular area of the image, such as central region 46 (FIG. 1B). Although the method as described herein relates to adjusting the gain applied to all the pixels in the image, the principles of this method may be used, alternatively or additionally, in adjusting regional gains that are applied to different areas of the image.

Upon detecting the change in brightness, processor 42 checks the topological characteristics of the region in which the distal end of insertion tube 30 is located, at a topology determination step 82. In the present example, the processor determines whether the distal end is inside lumen 26 or whether it is in chamber 24. The processor typically makes this determination automatically, by analyzing characteristics of the current image and possibly characteristics of a number of preceding images, as well. For example, the processor may analyze morphological and/or local brightness characteristics of the image. As another example, the processor may analyze changes in image brightness over the current and preceding images. Another method, based on image brightness and speed of the insertion tube in the body cavity, is described herein below with reference to FIG. 5. As noted above, the image brightness is expected to change only slowly within lumen 26, but may change rapidly as the endoscope approaches or moves away from the wall of chamber 24. The rate of change of brightness is thus indicative of the local topology. Additionally or alternatively, a user of system 20 may input information to the system, indicating when the endoscope is in lumen 26 and when it has entered chamber 24.

If processor 42 determines that the distal end of insertion tube is inside lumen 26 (or at some other location far from the wall of chamber 24), the processor may apply a normal gain control algorithm in determining the gain adjustment that is to be made in response to the current intensity change, at a normal gain control step 84. Typically, the gain to be applied in frame n+1 is determined by the gain in the preceding frame $g_s$ and by the change in image brightness $\Delta$ in an adaptive relation of the form: $g_{a-1} = g_N - \alpha \Delta^\gamma$, wherein $\alpha$ and $\gamma$ are predetermined constants. Under normal gain control, at step 84, $\alpha \ll 1$ and $\gamma \leq 1$. This control algorithm avoids rapid gain excursions that may be distracting to the eye of the user of system 20.

On the other hand, if processor 42 determines that the distal end of the insertion tube is approaching or receding from the chamber wall, it applies accelerated gain adjustment, at an accelerated gain control step 86. The accelerated gain adjustment takes into account the strong dependence (typically fourth-power, as explained above) of the brightness on the distance of the distal end from the chamber wall in order to predict the expected level of the image signals and to adjust the gain accordingly. For example, a Kalman filter or linear extrapolation may be applied to a sequence of image brightness measurements collected over a certain number of frames. Alternatively or additionally, an adaptive relation may be used, like the formula for $g_{a+1}$ given above, in which the values of $\alpha$ and/or $\gamma$ are increased substantially relative to the normal mode. The accelerated gain adjustment permits system 20 to adapt rapidly to the changes in brightness that occur when the insertion tube is facing the wall of chamber 24 or is approaching or receding from some other surface in cavity 22.

Figure 5:
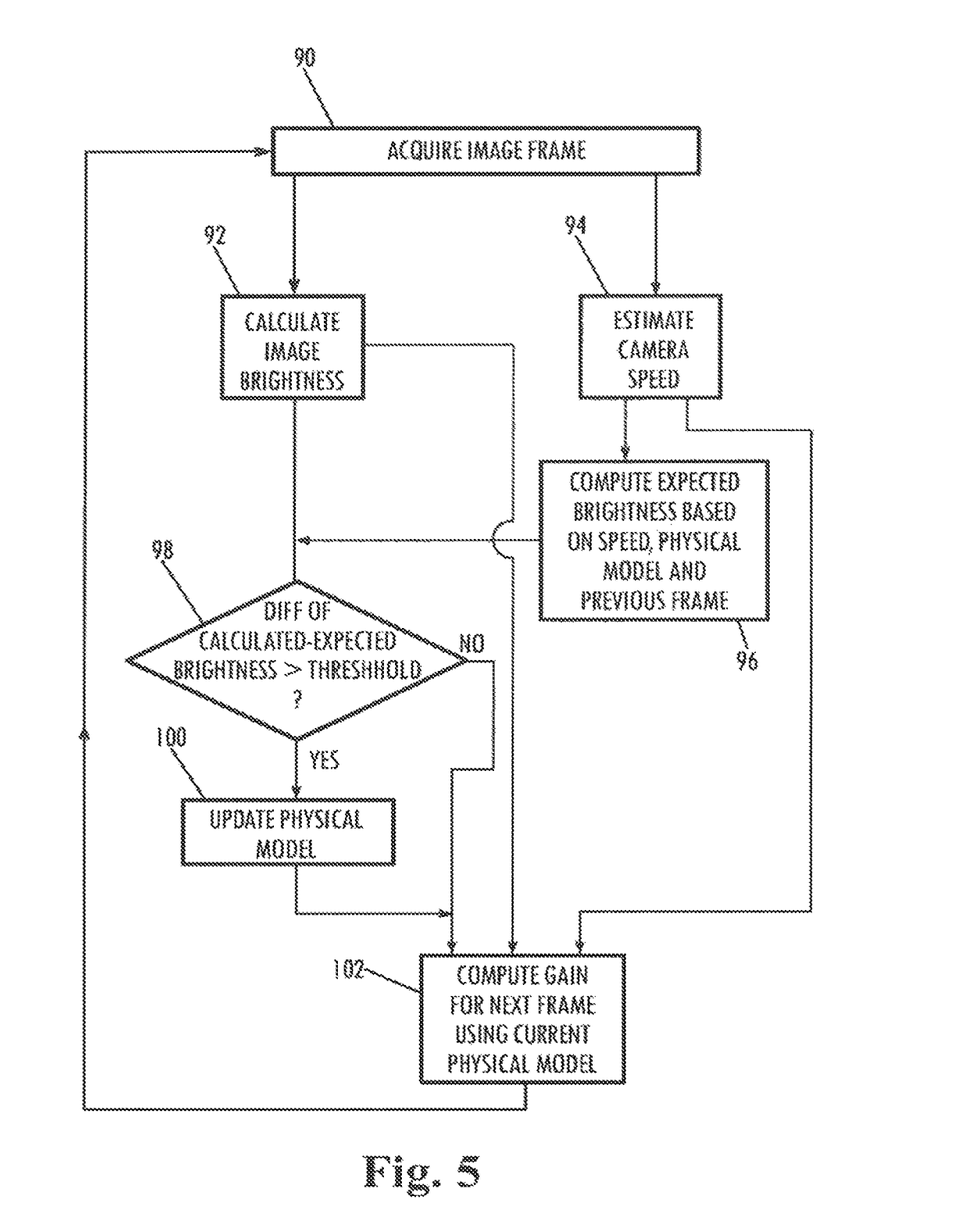
FIG. 5 is a flow chart that schematically shows details of a method for predictive control of image brightness, in accordance with an embodiment of the present invention.

FIG. 5 is a flow chart that schematically illustrates a method for performing predictive gain control in a changing physical environment, which may be used with the inventive subject matter described herein. The method is carried out following acquisition of each image frame, at an image acquisition step 90. Based on the image, control processor 42 calculates a measure of the image brightness, at a brightness measurement step 92. Any suitable statistical brightness measure may be used, as described above. The control processor also estimates the speed of motion of the insertion tube within the body cavity, at a speed estimation step 94. The speed may be estimated by means of image processing, for example, by identifying an image feature in one frame, and then detecting the change in position and/or size of the same feature in successive subsequent frames. Alternatively or additionally, the speed may be measured directly using a motion sensor, such as an accelerometer (not shown in the figures), in or coupled to the insertion tube.

Based on the estimated speed and on the brightness of the preceding frame or frames, processor 42 computes the expected brightness of the current frame, at a brightness prediction step 96. This computation is based on the current physical model (i.e., the topological model) of the part of the body cavity in which the insertion tube is located. In other words, if the insertion tube is located in lumen 26, it is expected that the brightness will change slowly from image to image, and processor 42 will thus apply a physical model that assumes slow variation of the brightness with the speed. For example, the expected brightness may be calculated as a linear function of the speed and the previous frame brightness. On the other hand, with chamber 24, image brightness is expected to vary with the inverse fourth power of the distance of the distal end of the insertion tube from the chamber wall. Therefore, processor 42 may apply a physical model in which the frame brightness varies roughly as the fourth power of the speed, weighted by the distance from the chamber wall.

Processor 42 compares the actual brightness of the current frame from step 92 to the expected brightness from step 96, at a brightness comparison step 98. If the difference between the brightness values is less than a predetermined threshold, the processor concludes that the current physical model is the correct one. Under these circumstances, the insertion tube is determined to have remained in the part of the body cavity (lumen of chamber) in which it was located previously. In this case, the processor goes on to calculate the gain to be applied to the next image frame based on the current physical model (lumen or chamber) and the current frame brightness, at a gain computation step 102.

If the difference between the actual and expected brightness at step 98 is greater than the threshold, however, processor 42 may determine that the insertion tube has moved into a region with a different topology. For example, if the actual brightness is significantly greater that the expected brightness while the insertion tube is moving forward, the processor may determine that the insertion tube has entered chamber 24 and is capturing images of the chamber wall. In this case, the processor changes the physical model that will be used in the gain computation, at a model update step 100. The gain for the next frame is computed accordingly at step 102, and the process continues from step 90.

Figure 6A:
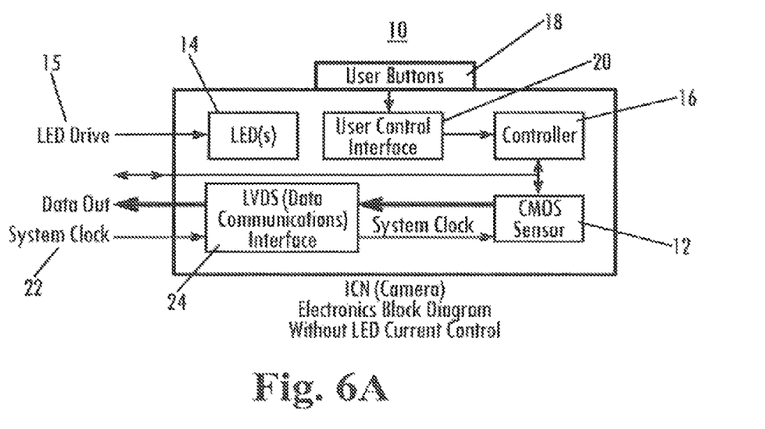
FIG. 6A is an electronics block diagram shown without an LED Current Control.

FIG. 6A shows an electronics block diagram for an imaging system 10 without control of current to an LED light system. The system includes an image sensor such as a CMOS sensor 12. The system includes a light source 14, such as one or more LEDs. An LED drive 15 for powering an LED is coupled to the one or more LEDs. One or more controllers or processors communicate with one or more system components to process data and instructions. In this block diagram a controller 16 communicates with a user interface subsystem comprising a manual control button 18 and a user control interface 20. A system clock 22 communicates with a data communications interface 24 and the image sensor.

Figure 6B:
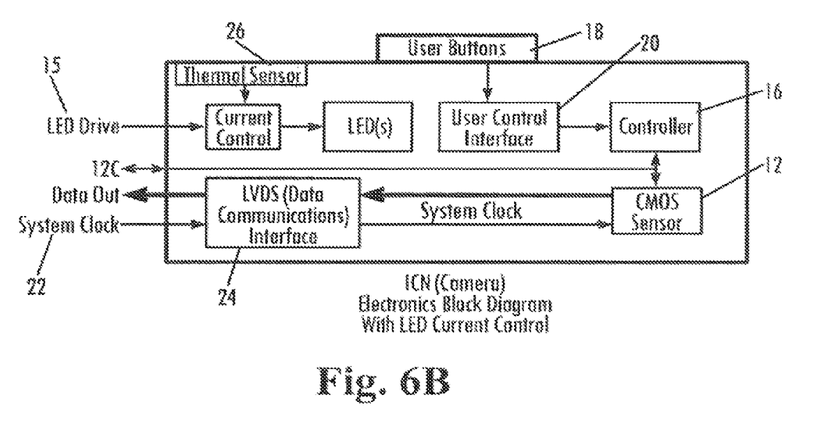
FIG. 6B is an electronics block diagram shown with an LED Current Control according to the inventive subject matter.
Figure 6C:
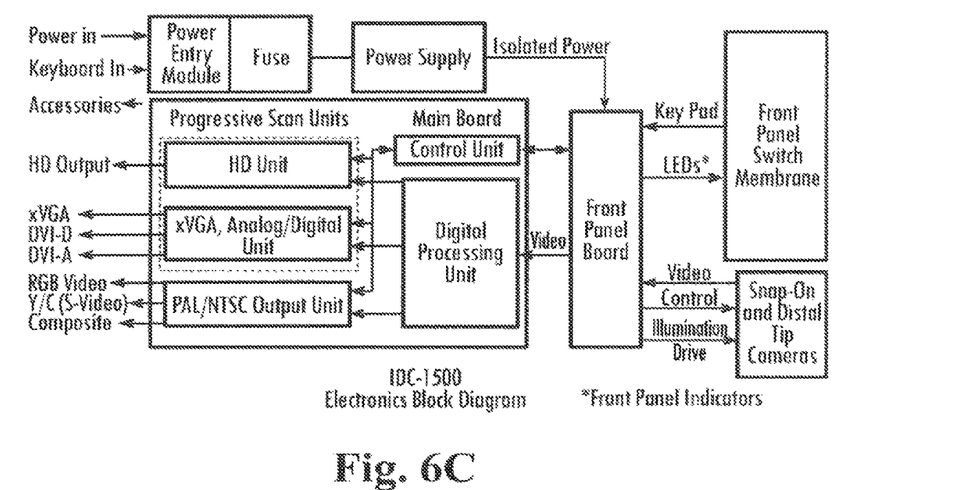
FIG. 6C is a sample electronic block diagram according to the inventive subject matter.

FIG. 6B shows the system 10 configured with a current controller 26 that controls the level of current provided via the LED drive 15. The current controller processes input from a sensor that monitors conditions that correlate with a state of the device in which system 10 is associated. For example, the sensor 26 may be temperature sensor that monitors the temperature of the handle of the device. The following section provides more details about such an example system.

Temperature Sensing Drive Control

A temperature sensing drive control for a light source, such as one or more LEDs, could be relatively simple transistor circuit which normally allows full current to pass through to the LED(s) but can act as a current limiter based on input from a temperature sensor mounted in the endoscope handle, designed to keep handle temperature below a predetermined level, for example about 40° C. In this and other embodiments, the current limiter could be controlled either in a binary on/off fashion or to provide variable current for a range of light output.

This system could be implemented in several ways. for example, in one possible approach the system would consist of a thermal sensor (thermistor, RTD, thermocouple, or hybrid IC) in good thermal contact with, for example, and endoscope handle. The CCU would then condition the signal from this sensor directly. The CCU software would then control or limit the drive to the LED to limit the maximum handle temperature. In the second approach a separate circuit in the endoscope itself would condition the signal from the thermal sensor. This circuit could consist of a standalone embedded controller or similar device. This device could run firmware or similar code to then control and monitor the LED drive current and regulate handle temperature independent of the CCU. A third approach would utilize the thermal sensor with the embedded controller in conjunction with the CCU and system software.

Inactivity Monitoring Drive Control

Figure 7:
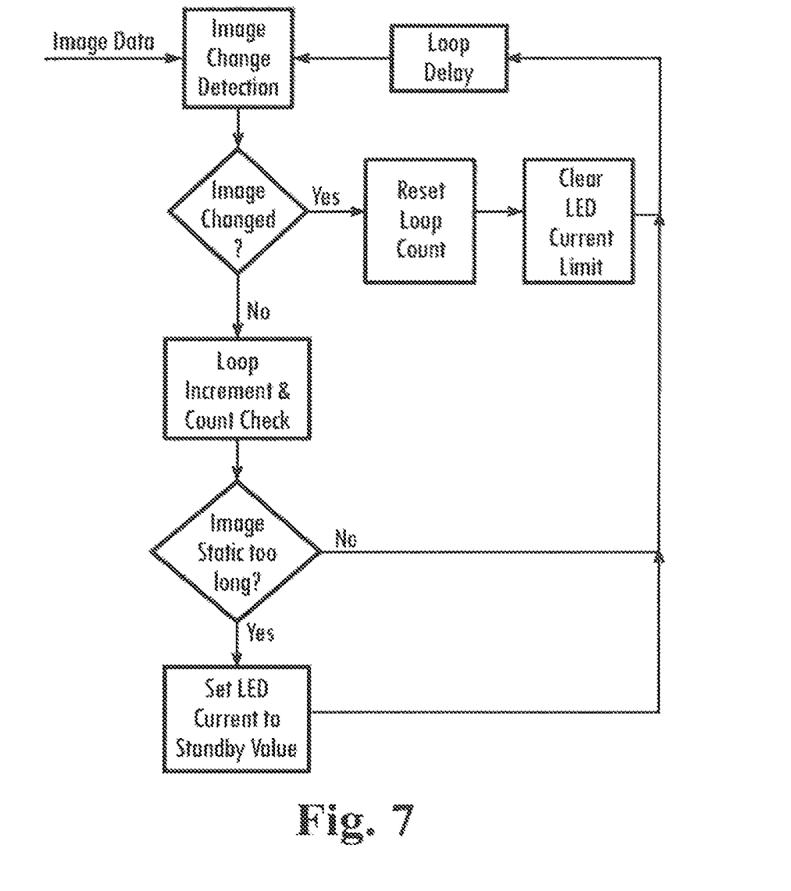
FIG. 7 is a flow chart showing one possible process for power control according to the inventive subject matter.

Referring particularly to FIG. 7, in another possible embodiment, machine executable instructions stored in an appropriate media would:
 a) have an inactivity timer running with a predetermined time limit
 b) be capable of sensing predetermined changes in the scene the sensor is detecting (either the entire area or in one or more areas of interest; could be limited to one or only a few predetermined pixels where in one possible implementation the value(s): if a new value exceeded the (appropriate) range then a scene change would be indicated)
 c) reset the inactivity timer when scene changes were detected
 d) if no scene changes were detected during the predetermined time limit, (perhaps also when the LED drive exceeded a threshold drive level) the LED drive level would be limited to a predetermined power level and there would be a continued monitoring for scene changes.
 e) if the inactivity power reduction mode was engaged and a scene change was detected, the limit on the LED drive level would be removed and the inactivity timer would be reset.

The stored instructions may be implemented in any of various known manners, such as software, firmware, or a FPGA.

Exemplary, systems and applications in which the inventive subject matter herein may be used include those disclosed by International Publication No. WO2006/032013, published Mar. 23, 2006, entitled "Endoscopy Device Supporting Multiple Input Devices," which is hereby incorporated by reference in its entirety. International Publication No. WO2006/032013 discloses, among other things a remote-head imaging system with a camera control unit capable of supporting multiple input devices. The camera control unit detects an input device to which it is connected and changes the camera control unit's internal functionality accordingly. Such changes include, for example, altering clock timing, changing video output parameters, and changing image processing software. In addition, a user is able to select different sets of software program instructions and hardware configuration information based on the head that is attached. The remote-head imaging system utilizes field-programmable circuitry, such as field programmable gate arrays (FPGA) in order to facilitate the change in configuration. This system would allow for the alteration or customization of power settings according to predetermined conditions.

Exemplary systems and applications in which the inventive subject matter may be used in include those disclosed by U.S. Publication No. US2005/0250983, published Nov. 10, 2005, entitled "Endoscopic Instrument Having Reduced Diameter Flexible Shaft," which is hereby incorporated by reference in its entirety. U.S. Publication No. US2005/0250983 discloses, among other things, a medical instrument comprising a flexible, filamentous shaft slideably disposed in a sheath, the instrument including an electronic imaging system comprising an image sensor carried on a distal end portion of the instrument. The shaft may be used as a guidewire for a complementary guided device, or it may be used to carry a functional element for performing a procedure at a target site in a patient's body. In other embodiments, the present invention contemplates a flexible sheath, preferably having a simple tubular construction, with an electronic imaging system at its distal end. The sheath is adapted to slideably receive a shaft, preferably a filamentous shaft, which closely fits the sheath. The shaft carries functional element at its distal end. The instruments according to the present invention may include one or more filaments along their length for deflecting an insertable portion of the instrument.

Exemplary systems and applications in which the inventive subject matter may be used in include those disclosed by U.S. Publication No. US2006/0173242, published Aug. 3, 2006, entitled "Hermetic Endoscope Assemblage," which is hereby incorporated by reference in its entirety. U.S. Publication No. US2006/01673242 discloses, among other things hermetically sealed enclosures and constructions for use in endoscopic systems, particularly endoscopic systems with electronic imaging and illumination systems in the enclosures. Compound optical windows are also disclosed for use in the systems. The compound optical windows may have separate panes for an imaging system and an illumination system, and contrast-reducing optical boundaries are between panes.

Persons skilled in the art will recognize that many modifications and variations are possible in the details, materials, and arrangements of the parts and actions which have been described and illustrated in order to explain the nature of this inventive concept and that such modifications and variations do not depart from the spirit and scope of the teachings and claims contained therein.

All patent and non-patent literature cited herein is hereby incorporated by references in its entirety for all purposes.

The invention claimed is:

1. A medical instrument comprising:
  a. one or more image sensors that monitor a state of activity;
  b. a lighting system for illuminating a target area, the system, comprising:
    i. a light source for illuminating an intracorporeal target area and
    ii. an associated power controller,
  wherein the power controller moves the lighting system from a first illumination mode to a second illumination mode based on an input into the lighting system of a predetermined condition from the one or more image sensors indicative of whether or not the instrument is in active use,
  wherein the input is a change in the state of activity or a lack of change in the state of activity;
  wherein the instrument senses a predetermined change of temperature; and
  wherein the predetermined change of temperature is the input into the lighting system so that the power controller makes a predetermined change in power to the light source based on the change in temperature.

2. The medical instrument of claim 1, wherein the instrument is a handheld instrument and the light source is disposed within a housing that comprises the handle of the instrument.

3. The medical instrument of claim 2, wherein the instrument is battery powered.

4. The medical instrument of claim 1, wherein the instrument comprises an endoscope having a solid state light source on or in the instrument for illuminating a target area.

5. The medical instrument of claim 4, wherein the light source is disposed in a handle portion of the endoscope.

6. The medical instrument of claim 4, wherein the light source is disposed in a distal insertion end of the endoscope.

7. The medical instrument of claim 4, wherein the one or more image sensors are disposed within a distal insertion portion of the endoscope.

8. The medical instrument of claim 1, wherein the medical instrument comprises an endoscope and the one or more image sensors are disposed within a distal insertion portion of the endoscope.

9. The medical instrument claim 1, wherein the system maintains a temperature of a surface of the instrument held or otherwise contacted by a user at a temperature of below about 40 degrees C.

10. The medical instrument of claim 1, wherein the input comprises a signal from a piezoelectric sensor or an accelerometer associated with the instrument.

11. The medical instrument of claim 1, wherein the state of activity is a change in scene.

12. The medical instrument of claim 1, wherein the medical instrument includes a timer and the power controller moves the lighting system from the first illumination mode to the second illumination mode when the change in scene has not occurred over a period of one minute.

13. The medical instrument of claim 1, wherein the medical instrument includes a processor that checks topological characteristics of a region proximal to the distal end of the endoscope so that the processor determines whether the distal end is inside a lumen or whether the distal end is within a chamber by analyzing characteristics of images from the one or more image sensors.

14. A medical instrument comprising:
  a. one or more image sensors that monitor a state of activity;
  b. a lighting system for illuminating a target area, the system, comprising:
    i. a light source for illuminating an intracorporeal target area and
    ii. an associated power controller,
  wherein the power controller moves the lighting system from a first illumination mode to a second illumination mode based on an input into the lighting system of a predetermined condition from the one or more image sensors indicative of whether or not the instrument is in active use,
  wherein the input is a change in the state of activity or a lack of change in the state of activity;
  wherein the image sensor includes a set of predetermined pixels that provide signals that are processed by a camera control unit to determine whether the state of activity that is monitored has a predetermined change;
  wherein the instrument senses a predetermined change of temperature; and
  wherein the predetermined change of temperature is the input into the lighting system so that the power controller makes a predetermined change in power to the light source based on the change in temperature.

15. The medical instrument of claim 14, wherein the medical instrument is a handheld instrument and the light source is disposed within a housing that comprises the handle of the instrument, and the instrument comprises an endoscope having a solid state light source on or in the instrument for illuminating a target area.

16. The medical instrument of claim 15, wherein the one or more image sensors are disposed within a distal insertion portion of the endoscope.

17. The medical instrument of claim 16, wherein the medical instrument includes a processor that checks topological characteristics of a region proximal to the distal end of the endoscope so that the processor determines whether the distal end is inside a lumen or whether the distal end is within a chamber by analyzing characteristics of images from the one or more image sensors.

18. The medical instrument of claim 14, wherein the medical instrument includes an insertion rube that is coupled to the camera control unit, and
   wherein video images generated by the camera control unit are displayed on a video display device.

19. The medical instrument of claim 14, wherein the one or more image sensors are disposed within a distal insertion portion of the endoscope.

20. The medical instrument of claim 14, wherein the medical instrument includes a processor that checks topological characteristics of a region proximal to the distal end of the endoscope so that the processor determines whether the distal end is inside a lumen or whether the distal end is within a chamber by analyzing characteristics of images from the one or more image sensors.

* * * * *

UNITED STATES PATENT AND TRADEMARK OFFICE
CERTIFICATE OF CORRECTION

| | |
|---|---|
| PATENT NO. | : 8,926,503 B2 |
| APPLICATION NO. | : 14/070865 |
| DATED | : January 6, 2015 |
| INVENTOR(S) | : Lawrence J. St. George |

It is certified that error appears in the above-identified patent and that said Letters Patent is hereby corrected as shown below:

On Title page 3, col. 2, line 32,

Please add under OTHER PUBLICATIONS the following art:

Japanese-language Office Action dated February 28, 2012, issued by the Japanese Patent Office in Japanese Application No.: 2008-1062393, 4 pages.
Office Action dated December 12, 2011 from the Patent Office in Germany Patent Application No.: 10392670.4, 9 pages.
Office Action dated June 17, 2011 from the Patent Office of Japan in Japanese Patent Application No. 2004-506277; 5 pages. English translation included.
Japanese Office Action dated May 19, 2011, for Japanese Patent Application No. 2010-278712 (Japanese language); 6 pages total. (English translation included).
Japanese Office Action dated April 26, 2011, for Japanese Patent Application No. 2008-106293 (Japanese language); 4 pages total. (Abridged English translation included).
Japanese Office Action dated March 18, 2009, for corresponding Japanese patent application number 2004-506277; English translation; 4 pages.
Japanese Office Action dated December 22, 2009, for a related Japanese Patent Application No. 2004-506277; 11 pages. English translation included.
Final Office Action dated May 28, 2010 from related U.S. Patent application number 10/514,607; 12 pages.
Non-Final Office Action dated July 22, 2009 from related U.S. Patent application number 10/514,607; 11 pages.
Non-Final Office Action dated November 24, 2009 from related U.S. Patent application number 10/514,607; 10 pages.
Japanese Office Action dated January 25, 2011, for a related Japanese Patent Application No. 2004-506277; 9 pages. English translation included.
Japanese Office Action dated August 17, 2010, for a related Japanese Patent Application No. 2004-506277; 6 pages. English translation included.

Signed and Sealed this
Twenty-first Day of April, 2015

Michelle K. Lee
*Director of the United States Patent and Trademark Office*

CERTIFICATE OF CORRECTION (continued)
U.S. Pat. No. 8,926,503 B2

United States Patent and Trademark Office Final Office Action dated November 9, 2010 for related U.S. Serial Number 11109041, filed April 18, 2005; 13 pages.
Examination Report from the German Patent and Trademark Office dated July 12, 2010 for related German patent application number 102008018931.6; informal English translation provided by German agent is included; 10 pages total.
U.S. Patent and Trademark Office Action dated May 22, 2009 for related U.S. patent application number 11/109,041 filed April 18, 2005; 21 pages.
Applicant's response to U.S. Patent and Trademark Office Action dated May 22, 2009 for related U.S. patent application number 11/109,041. Response filed August 19, 2009; 18 pages.

In the claims,

Column 13, Claim 18, Line 2, "rube" should be "tube"